United States Patent [19]

Sarantakis

[11] 4,215,039
[45] Jul. 29, 1980

[54] SOMATOSTATIN ANALOGUES

[75] Inventor: Dimitrios Sarantakis, West Chester, Pa.

[73] Assignee: American Home Products Corporation, New York, N.Y.

[21] Appl. No.: 12,430

[22] Filed: Feb. 15, 1979

[51] Int. Cl.$^2$ .................. C07C 103/52; C07G 7/00
[52] U.S. Cl. .......................... 260/112.5 S; 424/177
[58] Field of Search ........................... 260/112.5 S

[56] References Cited

U.S. PATENT DOCUMENTS

| | | | |
|---|---|---|---|
| 4,012,345 | 3/1977 | Sarantakis | 260/112.5 S |
| 4,076,659 | 2/1978 | Shields | 260/112.5 S |
| 4,077,952 | 3/1978 | Sarantakis | 260/112.5 S |

OTHER PUBLICATIONS

Rivier, J., et al., *Peptides 1976*, Proceedings of the Fourteenth European Peptide Symposium, pp. 427–451 (1976).

*Primary Examiner*—Delbert R. Phillips
*Assistant Examiner*—Blondel Hazel
*Attorney, Agent, or Firm*—Richard K. Jackson

[57] ABSTRACT

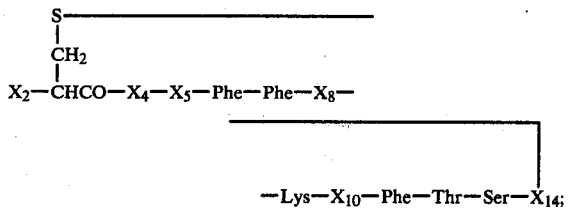

the linear precursor intermediates therefor or non-toxic acid addition salts thereof in which $X_2$ is H, $NH_2$, Ala—Gly—, Ala—D—Ala—, Gly—Gly—Gly—, lower alkanoyl or benzoyl;
$X_4$ is Arg, His or Lys;
$X_5$ is His, Tyr or Glu;
$X_8$ is Trp or D-Trp;
$X_{10}$ is Val, α-Abu, Leu, Phe or Tyr; and
$X_{14}$ is Cys, D-Cys or —$NH(CH_2)_2$—S—, inhibit the release of growth hormone and glucagon without substantial decrease in insulin and are useful in the treatment of acromegaly and diabetes.

7 Claims, No Drawings

SOMATOSTATIN ANALOGUES

BRIEF SUMMARY OF THE INVENTION

This invention provides certain somatostatin analogues selectively modified in 4, 5 and 10 positions, which are capable of suppressing release of growth hormone and glucagon without substantial decrease in insulin over periods approaching two hours. Thus, this invention resides in a group of novel polypeptides which are useful in the treatment of acromegaly and diabetes. The linear precursors for the novel polypeptides, either protected or deprotected, form an additional aspect of the invention.

DETAILED DESCRIPTION OF THE INVENTION

In accordance with this invention there is provided a group of polypeptides with long-lasting ability to inhibit release of growth hormone (somatotropin) and glucagon without substantial decrease in insulin release, which polypeptides are represented by the formula:

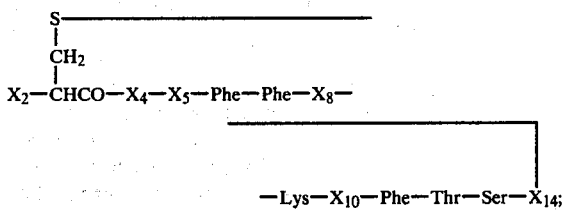

in which
X$_2$ is hydrogen, NH$_2$, Ala—Gly, Ala—D—Ala—, Gly—Gly—Gly—, lower alkanoyl or benzoyl;
X$_4$ is Arg, His or Lys;
X$_5$ is His, Tyr or Glu;
X$_8$ is Trp or D-Trp;
X$_{10}$ is Val, α-Abu, Leu, Phe or Tyr; and
X$_{14}$ is Cys, D—Cys or —NH(CH$_2$)$_2$—S—
or non-toxic acid addition salts thereof.

The non-toxic acid addition salts are pharmaceutically acceptable and are prepared from the polypeptide by conventional methods. Illustrative acids from which such salts are prepared include both organic and inorganic acids such as hydrochloric, hydrobromic, sulfuric, sulfonic, polyphosphoric, phosphoric, nitric, tartaric, fumaric, glycolic, citric, maleic, succinic, acetic, propionic, benzoic, ascorbic, and the like.

The lower alkanoyl N-terminal group embraces alkanoyl radicals of 2 to 6 carbon atoms, preferrably the acetyl group.

In accordance with an additional aspect of this invention there is provided a group of novel linear precursor intermediates useful in the preparation of the polypeptides described above, of the formula:

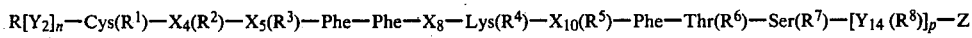

in which
R is hydrogen, an α-amino protecting group , lower alkanoyl or benzoyl;
R$^1$ and R$^8$ are hydrogen or a thio protecting group;
R$^2$ is hydrogen or a protecting group for N$^g$ of Arg, N$^{im}$ of His or the amino group of Lys;
R$^3$ is hydrogen or a protecting group for N$^{im}$ of His or the hydroxyl group of Tyr;
R$^4$ is hydrogen or an amino protecting group;
R$^5$ is hydrogen or a hydroxyl protecting group for Tyr;
R$^6$ and R$^7$ are hydrogen or a hydroxyl protecting group for Thr and Ser;
where
Y$_2$ is Ala—Gly—, Ala—D—Ala—or Gly—Gly—Gly—;
n is 0 or 1;
X$_4$ is Arg, His or Lys;
X$_5$ is His, Try or Glu;
X$_8$ is Trp or D-Trp;
X$_{10}$ is Val, α-Abu, Leu, Phe or Tyr;
Y$_{14}$ is Cys or D-Cys
p is 0 or 1
and
Z is —OH or —O—CH$_2$—[polystyrene resin support] with the proviso that R—R$^7$ are hydrogen when Z is —OH and R$^1$-R$^7$ are other than hydrogen when Z is —O—CH$_2$—[polystyrene resin support].

Illustrative of the applicable α-amino protecting groups represented by R are the groups:
formyl, trifluoroacetyl, phthalyl, toluenesulfonyl, o-nitrophenylsulfenyl, benzyloxycarbonyl, p-methoxybenzyloxycarbonyl, p-nitrobenzyloxycarbonyl, 2-bromobenzyloxycarbonyl, 2-chlorobenzyloxycarbonyl, 1-(p-biphenylyl)-1-methyl-ethoxycarbonyl, tertbutyloxycarbonyl, diisopropylmethoxycarbonyl, allyloxycarbonyl, 2,2,2-trichloroethoxycarbonyl, amyloxycarbonyl, α,α-dimethylbenzyloxycarbonyl, α,α-dimethyl-3,5-dimethoxybenzyloxycarbonyl, benzhydryloxycarbonyl, 9-fluoroenylmethoxycarbonyl, isobornyloxycarbonyl, adamantyloxycarbonyl.

Protecting groups R$^1$ and R$^8$ for the sulfhydryl group of the two cysteinyl moieties include:
benzyl, 3,4-dimethylbenzyl, p-methoxybenzyl, p-nitrobenzyl, p-chlorobenzyl, trityl, benzhydryl, tetrahydropyranyl, acetamidomethyl, t-butyl, ethylthio, ethylcarbamoyl, benzylthiomethyl or benzoyl;

Applicable R$^2$ protecting groups for the amino group of lysine are:
formyl, trifluoroacetyl, phthalyl, toluenesulfonyl, o-nitrophenylsulfenyl, benzyloxycarbonyl, p-methoxybenzyloxycarbonyl, p-nitrobenzyloxycarbonyl, 2-bromobenzyloxycarbonyl, 2-chlorobenzyloxycarbonyl, 1-(p-biphenylyl)-1-methyl-ethoxy carbonyl, tert-butyloxycarbonyl, diisopropylmethoxycarbonyl, allyloxycarbonyl, 2,2,2-trichloroethoxycarbonyl, amyloxycarbonyl, α,α-dimethylbenzyloxycarbonyl, α,α-dimethyl-3,5-dimethoxybenzyloxycarbonyl, benzhydryloxycarbonyl, 9-fluorenylmethoxycarbonyl, isobornyloxycarbonyl, adamantyloxycarbonyl; The selection of such a side chain amino protecting group is not critical except that it must be one which is not removed during cleavage of the α-amino protecting group during the synthesis until the peptide of the desired amino acid sequence is obtained. Hence, the α-amino protecting and side chain amino protecting group cannot be the same.

Protecting groups R$^2$ for Arg include:
nitro, tosyl, benzyloxycarbonyl, adamantyloxycarbonyl and tert-butyloxycarbonyl; preferably the tosyl group.

Protecting groups $R^2$ or $R^3$ for His include:

tosyl, benzyloxycarbonyl, adamantyloxycarbonyl and tert-butyloxycarbonyl; preferably the tosyl group.

Protecting groups $R^3$ or $R^5$ for Tyr include:

tert-butyl, trityl, benzyl, 2,6-dichlorobenzyl, benzyloxycarbonyl and 4-bromobenzyloxycarbonyl; preferably the 2,6-dichlorobenzyl or benzyl group.

The protecting groups $R^6$ and $R^7$ for the hydroxyl group of the threonyl and seryl moieties, may be benzoyl, tertbutyl or benzyl. The preferred protecting group for $R^6$ and $R^7$ is benzyl. The selection of these protecting groups is not critical except that they must not be removed during cleavage of the α-amino protecting group during the synthesis until the peptide of the desired amino acid sequence is obtained;

In selecting a particular side chain protecting group to be used in the synthesis of the peptides of this invention, the following rules should be followed: (a) the protecting group must be stable to the reagent and under the reaction conditions selected for removing the α-amino protecting group at each step of the synthesis; (b) the protecting group must retain its protecting properties (i.e. not be split off under coupling conditions, and (c) the side chain protecting group must be removable upon the completion of the synthesis containing the desired amino acid sequence under reaction conditions that will not alter the peptide chain.

The synthesis is commenced from the C-terminal end of the peptide by attaching α-amino protected and sulfhydryl protecting cysteine to a chloromethylated resin or a hydroxymethyl resin. The preparation of the hydroxymethyl resin is described by Bodanszky et al., Chem. Ind. (London) 38, 1597-98 (1966). A chloromethylated resin is commercially available from Lab. Systems, Inc., San Mateo, California and the preparation of such a resin is described by Stewart et al., "Solid Phase Peptide Synthesis" (Freeman & Co. San Francisco 1969), Chapter 1, pp. 1-6. The α-amino protected cysteine is coupled to the chloromethylated or hydroxymethyl resin with the aid of a carboyl group activating compound such as described by Kapoor, J. Pharm. Sci. 59, pp. 1-27 (1970) the disclosure of which is incorporated herein by reference. Following the coupling of the α-amino protected cysteine to the resin support, the α-amino protecting group is removed such as by using trifluoroacetic acid in methylene chloride, trifluoroacetic acid alone or HCl in dioxane. The deprotection is carried out at a temperature between about 0° C. and room temperature. Other standard cleaving reagents and conditions for removal of specific α-amino protecting groups may be used as described in Schroder & Lubke, supra, 1 pp. 72-75. After removal of the α-amino protecting group the remaining α-amino protected amino acids are coupled step-wise in the desired order. However, as an alternate to adding each amino acid separately to the reaction, some of them may be coupled prior to addition to the solid phase reactor. Each protected amino acid or amino acid sequence, is introduced into the solid phase reactor in about a four-fold excess and the coupling is carried out in a medium of dimethylformamide: methylene chloride (1:1) or in dimethylformamide or methylene chloride alone. In cases where incomplete coupling occurred the coupling procedure is repeated before removal of the α-amino protecting group, prior to the coupling of the next amino acid to the solid phase reactor. The success of the coupling reaction at each stage of the synthesis is monitored by the ninhydrin reaction as described by E. Kaiser et al., Analyt. Biochem., 34, 595 (1970).

After the desired amino acid sequence has been synthesized, the peptide is removed from the resin support by treatment with a reagent such as hydrogen fluoride which not only cleaves the peptide from the resin but also cleaves all remaining side chain protecting groups and the α-amino protecting group R to obtain the linear product. As an alternate route, the polypeptide linked to the resin support may be separated from the resin by methanolysis after which the recovered C-terminal methyl ester is converted to the acid by hydrolysis. Any side chain protecting group may then be cleaved by the procedure previously described or by other procedures such as catalytic reduction (eg. Pd on $BaSO_4$) using conditions which will keep the Trp moiety intact. When using hydrogen fluoride for cleaving, anisole is included in the reaction vessel to prevent the oxidation of labile amino acid (e.g. tryptophan). The linear deprotected polypeptide is converted to the cyclic disulfide by oxidation.

The solid phase synthesis procedure discussed supra, is well known in the art and has been essentially described by M. Monahan et al., C. R. Acad. Sci. Paris, 273, 508 (1971).

Where the C-terminal moiety is des-carboxycysteine $[X_{14}$ is $—NH(CH)_2—S—]$ the preparatory procedure is just as described above with the exception that the first amino acid residue introduced into the solid phase synthesizer is α-amino and hydroxy protected Ser. After construction of the amino acid sequence desired, the polypeptide is removed from the resin and the C-terminal seryl group is converted to the hydrazide by known methods. The hydrazide is then reacted with 2-mercaptoethylamine by conventional means to yield the linear intermediate which is oxidized to form the cyclic product of this invention.

The following examples illustrate the preparation of the compounds of this invention.

EXAMPLE 1 tert-Butyloxycarbonyl-S-p-methoxybenzyl-L-cysteinyl-N$^g$-tosyl-L-arginyl-N$^{im}$-tosyl-L-histidyl-L-phenylalanyl-L-phenylalanyl-D-tryptophyl-N$^ε$-2-chlorobenzyloxycarbonyl-L-lysyl-L-valyl-L-phenylalanyl-O-benzyl-L-threonyl-O-benzyl-L-seryl-S-p-methoxybenzyl-L:cysteinyl hydroxymethyl polystyrene ester Chloromethylated polystyrene resin (Lab. Systems Inc.) 1% cross-linked with divinylbenzene was esterified with Boc—Cys(SMBzl)—OH according to the procedure of Gisin, Helv. Chim. Acta, 56, 1976 (1973). The polystyrene resin ester was treated according to Schedule A for the incorporation of Boc-Ser(Bzl)OH, Boc—Thr(Bzl)OH, Boc—Phe—OH, Boc—Val—OH, Boc—Lys(ClZ)OH, Boc—D—Trp—OH, Boc—Phe—OH, Boc—Phe—OH, Boc—His(Tos)—OH, Boc—Arg(Tos)—OH, and Boc—Cys(SMBzl)OH, to afford the title peptidoresin.

Schedule A

1. Wash with $CH_2Cl_2 \times 3$.
2. Treat with TFA—$CH_2Cl_2$—EDT (1:1:5%, v/v) for 5 min.
3. Treat as in 2 for 25 min.
4. Wash with $CH_2Cl_2 \times 3$.
5. Wash with DMF.

6. Treat with 12% TEA in DMF twice for 3 min.
7. Wash with DMF.
8. Wash with $CH_2Cl_2 \times 3$.
9. Treat with 4 equivalents of the corresponding amino acid derivative in $CH_2Cl_2$—DMF and stir for 5 min.
10. Add in two portions 5 equivalents of DIC dissolved in $CH_2Cl_2$ and over a period of 30 min. Reaction time 6 hours.
11. Wash with DMF $\times 3$.
12. Wash with $CH_2Cl_2 \times 3$.
13. Test ninhydrin reaction according to Kaiser et al., *Annal. Biochem.* 34, 595 (1970). In case of incomplete reaction repeat lines 9 to 13 as above.

EXAMPLE 2

L-Cysteinyl-L-arginyl-L-histidyl-L-phenylalanyl-L-phenylalanyl-D-tryptophyl-L-lysyl-L-valyl-L-phenylalanyl-L-threonyl-L-seryl-L-cysteine cyclic (1-12) disulfide tetraacetate salt The peptidoresin of the previous Example (10 g) was mixed with anisole (20 ml) and treated with liquid HF in an ice-bath for 60 minutes. The excess HF was removed under vacuum as fast as possible and the residue was taken in dilute acetic acid and filtered. The filtrate was poured into 5 liters of deaerated water and the pH was adjusted with dilute $NH_4OH$ to 7, then a solution of $K_3Fe(CN)_6$ (2 g in 1 liter eater) was added dropwise until the yellow color was persistent for 15 minutes. The pH was adjusted to 5 with glacial acetic acid and the excess oxidant was removed by Bio Rad AG 3. The peptidic material was absorbed onto Amberlite (CG 50) and eluted with 50% aqueous acetic acid. The fractions containing peptidic material were lyophilized to the afford 837 mg. crude material. This crude material was applied onto a column ($2.5 \times 141$ cm) of Sephadex G-25 and eluted with 10% aqueous acetic acid. The material which emerged in fractions 111 to 131 (5.1 ml. each fraction) was pooled and lyophilized to yield 319 mg. of peptide. This material was applied onto a column ($1.5 \times 55$ cm) of Sephadex G 15 and eluted with 10% aqueous acetic acid. The material which emerged in fractions (4 ml. each) 25 to 35 was pooled and lyophilized to yield the desired title peptide (223 mg).

TLC, Avicel precoated glass plates. $R_f$(BWA, 4:1:1, v/v) 0.31, $R_f$(BWAP, 30:24:6:20, v/v)0.65.

Amino acid analysis, Thr (1) 0.83, Ser (1) 0.74, Cys (2) 0.99, Val (1) 0.99, Phe (3) 3, Lys (1) 1.05, His (1) 1.03, Trp (1) 0.96, Arg (1) 1.02.

EXAMPLE 3 tert-Butyooxycarbonyl-S-p-methoxybenzyl-L-cysteinyl-$N^g$-tosyl-L-arginyl-Y-benzyloxy-L-glutamyl-L-phenylalanyl-L-phenylalanyl-D-tryptophyl-$N^\epsilon$-2-chlorobenzyloxycarbonyl-L-lysyl-L-$\alpha$-aminobutyryl-L-phenylalanyl-O-benzyl-L-threonyl-O-benzyl-L-seryl-S-p-methoxybenzyl-L:cysteinyl hydroxymethyl polystyrene ester.

The above peptodoresin was prepared by the procedure set forth in Example 1.

EXAMPLE 4

L-Cysteinyl-L-arginyl-L-glutamyl-L-phenylalanyl-L-phenylalanyl-D-tryptophyl-L-lysyl-L-$\alpha$-aminobutyryl-L-phenylalanyl-L-threonyl-L-seryl-L-cysteine cyclic (1→12) disulfide The compound obtained in Example 3 was deprotected, cyclized and purified in a manner set forth in Example 2. TLC: Avicel precoated glass plates. $R_f$ (n-Butanol-water-gl. acidic acid, 4:1:1, v/v) 0.36., $R_f$ (n-Butanol-water-gl. acidic acid, 4:5:1, v/v) 0.42., $R_f$ (tert-Amylalcohol-pyridine-water, 7:7:6, v/v) 0.68.

Amino acid analysis: Thr(1) 0.89, Ser(1) 0.93, Glu(1) 1.02, Cys(2) 1.68, Phe(3) 3, Lys(1) 1.03, Trp(1) 0.86, Arg(1) 1,Abu N.D.

The in vivo activity of the polypeptides of this invention was established by subjecting the product of Example 2, as a representative compound of the invention, to the following standard test procedure: Two groups of ten albino male rats were arranged to provide a control group and a group for study of the product of Example 2. Nembutal (50 mg/kg) was injected intraperitoneally into each rat. Fifteen minutes later a subcutaneous injection of the test compound or physiological saline (control) was administered separately to each of the two groups of rats. Ten minutes later 0.5 milliliters of arginine (300 mg/ml, pH 7.2) was injected into the rats heart. The rats were decapitated five minutes later and their blood was collected in Trasylol-EDTA. Aliquot samples were radioimmunoassayed for growth hormone, insulin and glucagon. The results of these tests are presented below:

| Compound | Dose µg/kg | GH ng/ml | Insulin µg/ml | Glucagon pg/ml |
| --- | --- | --- | --- | --- |
| Control | — | 407±62 | 271±44 | 45±5 |
| Ex. 2 | 200 | 119±40 | 191±43 | 22±* |
| Control | — | 202±11 | 238±23 | 85±6 |
| Ex. 2 | 50 | 92±8* | 149±23 | 20±4 |

*p<0.01

The procedure described in the preceding paragraph was repeated with the exception that a ninety minute period was allowed to elapse before blood sampling. The results of this test is presented below:

| Compound | Dose µg/kg | Time | GH ng/ml | Ins µU/ml |
| --- | --- | --- | --- | --- |
| Control | — | 90 min. | 374±48 | 733±46 |
| Ex. 2 | 2,000 | 90 min. | 100±29* | 586±54+ |

*p<0.01
+p<0.05

Thus, the product of Example 2, [des-Ala$^1$-Gly$^2$, Arg$^4$, His$^5$, D-Trp$^8$, Val$^{10}$]somatostatin, at doses as high as 200 µg/kg is specific for the suppression of glucagon and growth hormone without affecting insulin secretion. At a dose of 2,000 µg/kg the product of Example 2 shows activity against growth hormone for a period of ninety minutes. These results are representative of the activities of the other compounds embraced by this invention.

Following the same procedure detailed above, the product of Example 4 gave the following results:

| Compound | Dose µg/kg | GH ng/ml | Insulin µU/ml | Glucagon pg/ml |
| --- | --- | --- | --- | --- |
| Control | — | 268±46 | 323±28 | 379±109 |
| Ex. 4 | 200 | 120±19* | 231±32+ | 40±19+ |

*p<0.01
+p<0.05

Thus, the compounds of this invention are effective in the treatment of conditions involving excessive secretion of somatostropin. From the known relationship between growth hormone control in standard experimental animals and the human, the activity of the disclosed peptides characterizes them as useful in the treatment of acromegaly and diabetes were administration with or without conjoint insulin therapy improves glucose homeostasis. Administration of the peptides may be by conventional routes common to somatostatin and related polypeptides, under the guidance of a physician in an amount dictated by the extent of the dysfunction as determined by the physician. The compounds may be administered alone or in conjunction with conventional pharmaceutically acceptable carriers and adjuvants, in unit dosage form containing from about 0.05 to about 100 milligrams per kilogram host body weight.

If the active ingredient is administered in tablet form the tablet may contain: a binder such as gum tragacanth, corn starch, gelatin, and excipient such as dicalcium phosphate; a disintegrating agent such as corn starch, alginic acid, etc.; a lubricant such as magnesium stearate; and a sweetening and/or flavoring agent such as sucrose, lactose, wintergreen, etc. Suitable liquid carriers for intravenous or subcutaneous administration include isotonic saline, phosphate buffer solutions, etc.

What is claimed is:

1. A compound of the formula:

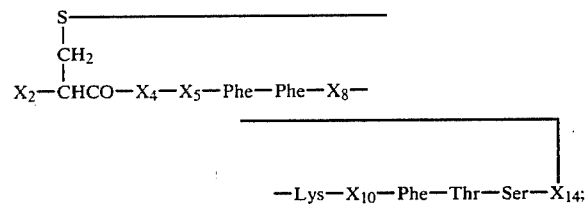

its linear precursor intermediates or non-toxic acid addition salts thereof in which $X_2$ is H, $NH_2$, Ala—Gly—, Ala—D—Ala, Gly—Gly—Gly—, lower alkanoyl or benzoyl;

$X_4$ is Arg, His or Lys;

$X_5$ is His, Tyr or Glu;

$X_8$ is Trp or D—Trp;

$X_{10}$ is Val, α—Abu, Leu, Phe or Tyr; and $X_{14}$ is Cys, D—Cys or —NH(CH$_2$)$_2$—S—.

2. The compound of claim 1 in which $X_{10}$ is Val, α-Abu or Leu.

3. The compound of claim 1 which is [des—Ala$^1$—Gly$^2$, Arg$^4$, His$^5$, D-Trp$^8$, Val$^{10}$]somatostatin.

4. The compound of claim 1 which is [des—Ala$^1$—Gly$^2$, Arg$^4$, Glu$^5$, D-Trp$^8$, α-Abu$^{10}$]somatostatin.

5. A compound of Claim 1 of the formula:

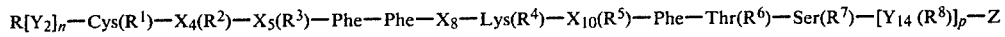

$R[Y_2]_n$—Cys($R^1$)—$X_4$($R^2$)—$X_5$($R^3$)—Phe—Phe—$X_8$—Lys($R^4$)—$X_{10}$($R^5$)—Phe—Thr($R^6$)—Ser($R^7$)—[$Y_{14}$($R^8$)]$_p$—Z in which R is hydrogen, an α-amino protecting group, lower alkanoyl or benzoyl;

$R^1$ and $R^8$ are hydrogen or a thio protecting group;

$R^2$ is hydrogen or a protecting group for N$^g$ of Arg, N$^{im}$ of His or the amino group of Lys;

$R^3$ is hydrogen or a protecting group for N$^{im}$ of His or the hydroxyl group of Tyr;

$R^4$ is hydrogen or an amino protecting group;

$R^5$ is hydrogen or a hydroxyl protecting group for Tyr;

$R^6$ and $R^7$ are hydrogen or a hydroxyl protecting group for Thr and Ser;

where $Y_2$ is Ala—Gly—, Ala—D—Ala—or Gly—Gly—Gly—;

n is 0 or 1;

$X_4$ is Arg, His or Lys;

$X_5$ is His, Tyr or Glu;

$X_8$ is Trp or D-Trp;

$X_{10}$ is Val, α-Abu, Leu, Phe or Tyr;

$Y_{14}$ is Cys or D-Cys;

p is 0 or 1 and

Z is —OH or —O—CH$_2$—[polystyrene resin support] with the proviso that R—$R^7$ are hydrogen when Z is —OH and $R^1$-$R^7$ are other than hydrogen when Z is —O—CH$_2$—[polystyrene resin support].

6. The compound of claim 1 which is tert-Butyloxycarbonyl-S-p-methoxybenzyl-L-cysteinyl-N$^g$-tosyl-L-arginyl-N$^{im}$-tosyl-L-histidyl-L-phenylalanyl-L-phenylalanyl-D-tryptophyl-N$^ε$-2-chlorobenzyloxycarbonyl-L-lysyl-L-valyl-O-benzyl-L-threonyl-O-benzyl-L-seryl-S-p-methoxybenzyl-L-cysteinyl hydroxymethyl polystyrene ester.

7. The compound of claim 1 which is tert-Butyloxycarbonyl-S-p-methoxybenzyl-L-cysteinyl-N$^g$-tosyl-L-arginyl-Y-benzyloxy-L-glutamyl-L-phenylalanyl-L-phenylalanyl-D-tryptophyl-N$^ε$-2-chlorobenzyloxycarbonyl-L-lysyl-L-ε-aminobutyryl-L-phenylalanyl-O-benzyl-L-threonyl-O-benzyl-L-seryl-S-p-methoxybenzyl-L-cysteinyl hydroxymethyl polystyrene ester.

* * * * *

UNITED STATES PATENT OFFICE
CERTIFICATE OF CORRECTION

Patent No. 4,215,039                Dated July 29, 1980

Inventor(s) Dimitrios Sarantakis

It is certified that error appears in the above-identified patent and that said Letters Patent are hereby corrected as shown below:

Column 8, line 38, delete "toxyl" and insert --tosyl--;

Column 8, line 40, after "L-valyl" insert --L-phenylalanyl--;

Column 8, line 45, delete "Y" and insert --Y--.

Signed and Sealed this

Eighteenth Day of November 1980

[SEAL]

Attest:

SIDNEY A. DIAMOND

Attesting Officer            Commissioner of Patents and Trademarks